(12) United States Patent
Bargh et al.

(10) Patent No.: US 10,329,524 B2
(45) Date of Patent: Jun. 25, 2019

(54) BIOREACTOR CONSUMABLE UNITS

(71) Applicant: TAP BIOSYSTEMS (PHC) LIMITED, Royston, Hertfordshire (GB)

(72) Inventors: Adrian Neil Bargh, Royston (GB); Adrian James Stacey, Cambridge (GB); Sean Kenneth Sullivan, Baldock (GB)

(73) Assignee: THE AUTOMATION PARTNERSHIP (CAMBRIDGE) LTD., Royston, Hertfordshire (GB)

( * ) Notice: Subject to any disclaimer, the term of this patent is extended or adjusted under 35 U.S.C. 154(b) by 458 days.

(21) Appl. No.: 14/901,390

(22) PCT Filed: Jun. 27, 2014

(86) PCT No.: PCT/GB2014/051971
§ 371 (c)(1),
(2) Date: Dec. 28, 2015

(87) PCT Pub. No.: WO2015/001321
PCT Pub. Date: Jan. 8, 2015

(65) Prior Publication Data
US 2016/0152936 A1 Jun. 2, 2016

(30) Foreign Application Priority Data
Jul. 1, 2013 (GB) .................................. 1311775.9

(51) Int. Cl.
C12M 1/00 (2006.01)
C12M 3/00 (2006.01)
(Continued)

(52) U.S. Cl.
CPC ............ *C12M 23/44* (2013.01); *C12M 23/30* (2013.01); *C12M 23/42* (2013.01); *C12M 23/48* (2013.01);
(Continued)

(58) Field of Classification Search
CPC ....... C12M 23/14; C12M 23/28; C12M 41/48
See application file for complete search history.

(56) References Cited

U.S. PATENT DOCUMENTS 4,396,385 A * 8/1983 Kelly .................... A61M 5/172
128/DIG. 12
5,652,143 A 7/1997 Gombrich et al.
(Continued)

FOREIGN PATENT DOCUMENTS

EP 2 270 129 A2 1/2011
GB 2 495 934 A 5/2013
JP 2008 079554 A 4/2008

*Primary Examiner* — William H. Beisner
(74) *Attorney, Agent, or Firm* — Dickinson Wright PLLC

(57) ABSTRACT

A bioreactor consumable unit (50; 500) comprises a bioreactor part (60); a fluid feed container part (80) integrally connected with the bioreactor part and including at least one fluid feed container (82) in fluid communication with the bioreactor (60); and an integral pumping element (100, 110; 160, 206) configured to enable fluid to flow from the at least one fluid feed container (82) to the bioreactor (60). The bioreactor part (60) includes a bioreactor chamber (62) and a stirrer (64) for agitation of a cell culture (66) in the chamber. The pumping element comprises a combination of a syringe pump (110) and an associated three-way valve (102). The bioreactor consumable unit (50; 500) may be inserted into a receiving station (20) of a cell culture module (10) for the processing and control of a bioreaction in the bioreactor chamber (62). The provision of the fluid feed containers (82) and the pumping element (100, 110; 60, 206) as integral parts of the bioreactor consumable unit (50; 500)

(Continued)

facilitates the set-up of the processing, because the various fluid connections between those components are already established. The syringe pump (110) provides accurate dispensing of fluids to the bioreactor chamber (62).

37 Claims, 11 Drawing Sheets

(51) Int. Cl.
    *C12M 1/06*     (2006.01)
    *C12M 1/26*     (2006.01)
    *C12M 1/12*     (2006.01)
    *C12M 1/34*     (2006.01)

(52) U.S. Cl.
    CPC ............ *C12M 23/58* (2013.01); *C12M 27/02* (2013.01); *C12M 29/00* (2013.01); *C12M 33/04* (2013.01); *C12M 37/02* (2013.01); *C12M 41/34* (2013.01); *C12M 41/42* (2013.01)

(56) References Cited

U.S. PATENT DOCUMENTS

| | | | |
|---|---|---|---|
| 7,255,680 B1 * | 8/2007 | Gharib | ................ A61M 5/1483 |
| | | | 604/67 |
| 7,906,323 B2 * | 3/2011 | Cannon | .................. C12M 23/42 |
| | | | 435/287.1 |
| 2010/0159577 A1 | 6/2010 | Tokumaru | |
| 2010/0317093 A1 | 12/2010 | Turewicz et al. | |
| 2012/0122138 A1 * | 5/2012 | Randles | ................. C12M 23/14 |
| | | | 435/29 |
| 2012/0264210 A1 * | 10/2012 | Bontinck | ............... C12M 29/14 |
| | | | 435/366 |

\* cited by examiner

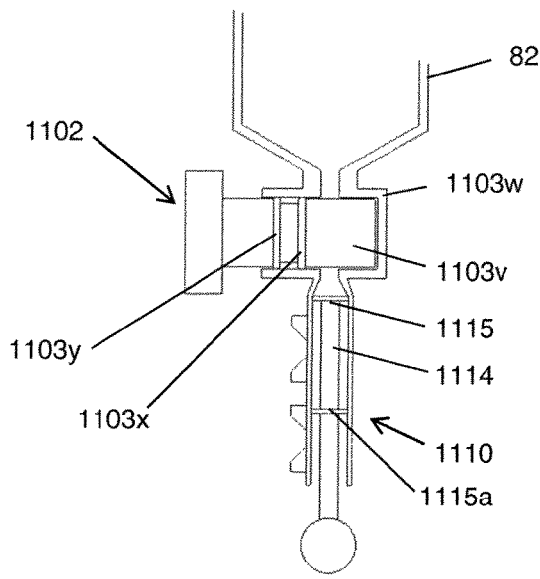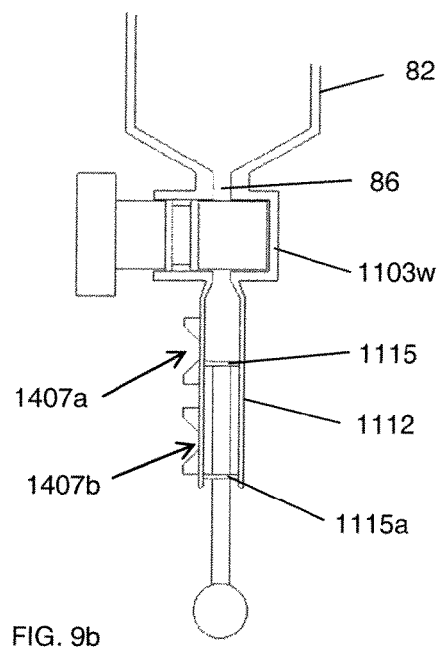
FIG. 9a  FIG. 9b
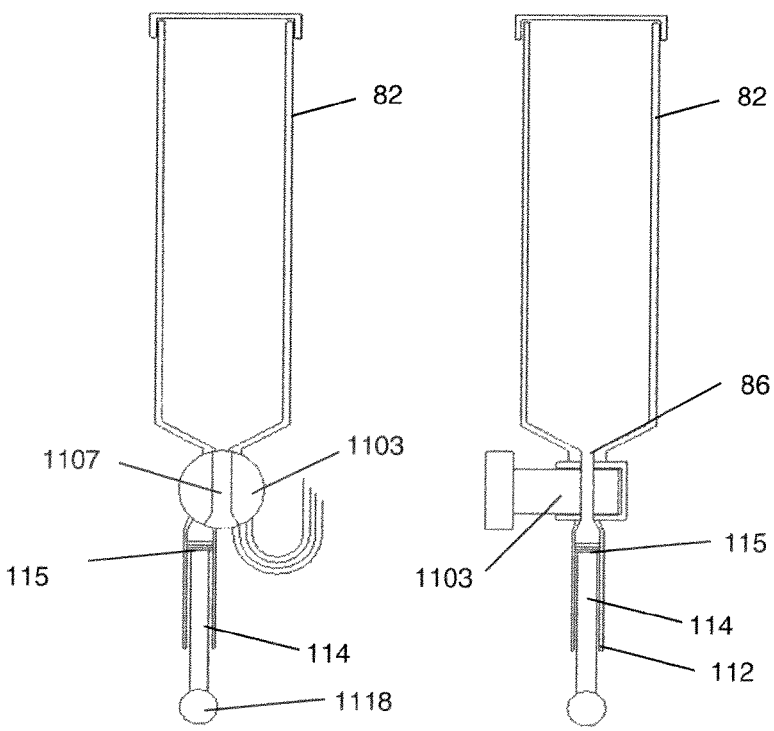
FIG. 10a  FIG. 10b

BIOREACTOR CONSUMABLE UNITS

FIELD OF THE INVENTION

The invention relates generally to the field of bioreactor processing systems for cell cultures. More particularly, the invention concerns bioreactor consumable units, to improve the handling and set-up of bioreactors and their associated fluid feeds Throughout this document, the term 'cell culture' is to be understood as encompassing not only mammalian cell cultures, but also insects, algae, plants and microbial cell cultures (fermentation) and any other cell types, as well as other biochemical or cellular processes such as, but not limited to biotransformations, transfection, transient protein expression, cell-free biological systems. However, this invention could also be used for other, non-biological, processes.

BACKGROUND TO THE INVENTION

Cell cultures, consisting of cells growing suspended in a growth media, or on the surface of suspended particles, in solution are produced within bioreactors with careful control of a number of parameters. These bioreactors may be capable of processing large quantities of cell culture solution. For example, large-scale bioreactors can have capacities from 1-20,000 liters, or even up to 50,000 liters.

Within the bioreactor it is important to carefully control the environment to which the cells are exposed. Subtle changes in the environment can have major effects on the physiology of the cells and the amount of the target product (product titre), for example a recombinant protein, that is produced by each cell. This in turn has a major impact on the economics of the production process. The parameters that must be controlled include the concentrations of oxygen and carbon dioxide available to the cells (dissolved oxygen and $CO_2$), pH, temperature, and specific nutrient levels such as the concentration of glucose. Additionally the physical environment is critical; particularly important components including the form of the gas distribution e.g. bubble size and overall gas flow. Finally, the mixing of the liquid and cells is critical having an impact on the homogeneity within the reactor and hence the local environmental variation to which cells within a bioreactor are exposed. Such issues become significant in very large bioreactors.

A major challenge facing companies manufacturing products in bioreactor systems is the optimisation of the conditions within a bioreactor for the production of a particular product. Optimisation of conditions for a particular cell line producing a particular product can easily have magnitude level effects on the yield of the product, this in turn having a massive impact on the economics of production. Addressing this issue is not simple; there are many parameters to be controlled and the optimal approach may involve variations in these conditions over time. However, it is impractical to explore the impact of varying a range of parameters due to the lack of availability of equipment and the huge costs of operation. The actual costs of one run of a 2 l bioreactor can be over $2000. At larger scales the cost rapidly becomes prohibitive. Such issues prevent the application of modern statistical based experiment approaches to resolving the impact of multiple parameter variation typically referred to as DOE (Design of Experiment), such approaches typically requiring tens of bioreactor experiments to have value.

The opportunity for such work to have value has increased over recent years as regulatory authorities have introduced initiatives in which variations within a production run do not necessarily mean the automatic failure of a batch IF the impact of such variations in control parameters has previously been explored. This is impossible without small-scale highly parallel models of bioreactors but essential for manufacturers to remain competitive.

A further issue faced is the difficulty of selecting cell lines early in development that are robust and productive in a stirred bioreactor environment. Clearly, where high tens to hundreds of cell lines need to be screened, existing bioreactor systems are impractical.

A number of small-scale approach bioreactors have been tried, e.g. shaken multiwell plates and flasks, but these lack the ability to faithfully reproduce the conditions found in stirred, gassed systems with closed loop control of culture parameters. To date, small-scale experiment runs are generally carried out in individual bioreactors, of 1 to 10 liter capacity, containing cell cultures in solution. These are processed under careful, monitored control for a period of about two weeks. During that period, the input parameters discussed above may be varied between the individual bioreactors, with the contents of the respective bioreactors being monitored so as to determine which set of parameters achieves optimum, desired results. That set of parameters can then be used in order to scale-up the process to full production scale; the objective being to maximise cell production or cell viability, to improve production efficiency and/or to increase product titre yield.

Control of the culture parameters is required from three perspectives: i) the maintenance of a parameter at a defined set-point, within control limits, for a given time; ii) the controlled, planned variation of that parameter over time; and finally iii) the consistency and reproducibility of that parameter from bioreactor to bioreactor and run to run. Once such control is achieved, parameters can be varied and the impact of the variation on productivity determined.

The cell culture solution within a bioreactor may be stirred in order to ensure homogeneity. The rate of stirring can have a major impact on the productivity of the culture through the impact of the physical environment of the cells, for example shear, on the viability and productive life of the cells. Additionally, the stirring rate has a direct effect on mixing and therefore the efficiency of mass transfer of gasses from the input stream of bubbles into the liquid phase where it is available to the cells. The balance between stir rates and their potential negative effects and the benefits of good mixing and gas transfer must be established for a particular culture. At manufacturing scale, energy inputs to the reactor additionally become an important economic consideration.

In many existing small-scale systems, the contents of the bioreactor vessels are not stirred, but are instead agitated by shaking. Whereas this simplifies the system, the vessels not requiring individual stirrers, it does not produce accurate simulation of production scale conditions, in which the contents are stirred; shaking does not replicate the shear forces induced in the vessel contents by stirring. Additionally, gas transfer in shaken vessels is primarily through surface aeration rather than bubbles fed into the base of the system, altering the dynamics of the gas transfer and the physical environment.

As described in co-pending European patent application publication no. 2270129, from the same applicant, which describes a micro-scale bioreactor system for faithful reproduction of parameters within larger scale bioreactors, the cell culture solution within the bioreactor is stirred in order to ensure homogeneity. The rate of stirring can have a major impact on the productivity of the culture through the impact of the physical environment of the cells, for example shear, on the viability and productive life of the cells. Additionally, the stirring rate has a direct effect on mixing and therefore the efficiency of mass transfer of gasses from the input stream of bubbles into the liquid phase where it is available to the cells. The balance between stir rates and their potential negative effects and the benefits of good mixing and gas transfer must be established for a particular culture. At manufacturing scale, energy inputs to the reactor additionally become an important economic consideration.

There are two key aspects to the gas control within bioreactors: that of $CO_2$ and that of $O_2$.

The dissolved oxygen level in the bioreactor must be maintained at a set level to ensure a consistent availability to the cells such that metabolism is not limited. Typical maintenance levels vary between 15 and 50% of the maximum dissolved oxygen level achieved by air saturation. Approaches to achievement of this vary between users, some preferring to use lower input concentrations and higher flow rates, others higher input concentrations and lower flow rates. Control of the input flow rate is critical as it affects the stripping of other gases such as $CO_2$ from the culture media.

The concentration of $CO_2$ that the cells are exposed to can have significant effects on metabolism. Control of $CO_2$ is additionally used to control pH in combination with bicarbonate based buffer systems in the media. Bubbles are also a key source of damage to cells and hence control of the total gas inflow rate is an important factor in maintaining cell viability.

The pH level within the bioreactor should remain within predetermined bounds, which can vary as the cell culture develops. Generally this is achieved by a combination of a bicarbonate based buffer system within the liquid media, combined with the maintenance of a specific level of dissolved $CO_2$. However, above a certain cell density the production of lactic acid by the cells can overwhelm the buffering capability of the media and the pH is maintained within the desired limits by the addition of doses of alkali solutions to combat the increasing acidity. The addition of alkali in bioreactors is controlled as part of a feedback loop including a pH sensor.

Temperature is an important parameter within bioreactors. The temperature used within bioreactors culturing mammalian cells does not vary widely due to the origins of the cells in animals exhibiting control of body temperature. However, some minor variations are used during the period of culture, to effect shifts in metabolism biasing the cell physiology towards production of the recombinant protein rather than cell multiplication for example. For microbial cultures, the operating temperature may vary, dependent on the organism, between 18-65° C. and needs to be controlled accurately.

Generally, a heater is controlled in order to increase or decrease the amount of supplied heat. In some systems, the culture growth and energy inputs into stirring generate excess heat, so cooling and heat dissipation systems are required.

Monitoring of various parameters within the bioreactor is key to their control. Some parameters are controlled through closed loop sensing and response systems, others through sampling and off-line analysis due to the lack of appropriate on-line monitoring systems.

A range of nutrient feeds may be dispensed into the reactor. Typically these include media feeds which supply additional amino acids and carbon sources to replace those used in cell growth. Multiple different feeds may be added to a bioreactor on different schedules, often including pure carbon sources such as glucose. Generally, such feeds are added in response to the measurement of parameter levels within the bioreactor.

In addition, reactors are often connected to supplies of acid and base (alkali) in order to control the cell processes within. Also, a supply of anti-foaming agent may be connected to a reactor to minimise the foaming caused by the stirring of the liquid.

It is time-consuming and often manually complex for an operator to connect and disconnect the fluid conduits to the respective inlet/outlet ports so as to establish the multiple fluid pathways for the input of gases and/or nutrients and/or acid, base and anti-foaming agents into the bioreactor.

In EP2270129, the process was improved by enabling the connection of multiple fluid pathways in a single step through use of a common clamp plate defining respective conduits between the inlet/outlet ports of the respective vessels and associated fluid ports in a base station. However, a drawback of this approach is that fluids can remain in the conduits of the clamp plate between experiment runs, risking contamination of subsequent runs—particularly in the case of the nutrient feed. This problem may be overcome by flushing out and/or sterilising the conduits between runs, but that adds an additional step to the process.

Another system and method for making the fluid connections is described in co-pending GB patent application no. 1213506.7, in which the connections are made automatically on insertion of a bioreactor consumable unit into an associated receiving station.

Moreover, the bioreactor system must remain sterile, which requires the different nutrient feeds to be supplied from sterile sources. Typically, fluid feed containers have been loaded with the nutrients—for example within a laminar flow hood—at the point of use of the bioreactor, with the loaded fluid feed containers being connected up to the bioreactor under sterile conditions. One exemplary known way to make such connections in a sterile manner outside of laminar flow hoods is through the use of tube welders, which are for cutting and thermally fusing two previously unconnected thermoplastic tubes in a sterile welding operation. To perform the operation multiple times, on the various different lines of tubing needed to connect the multiple sources to the bioreactor can be complicated, time-consuming and relatively expensive.

Various attempts have been made to incorporate fluid feed reservoirs and associated pumping elements into bioreactors. The pumping elements have typically been peristaltic pumps, gear pumps, diaphragm, piston pumps or other flow-through pumps. Examples include those described in US 2011/0130310 A1, U.S. Pat. No. 6,670,169 B1, JP 2010-142196 A1, WO 2007/044699 A1, US 2005/0186671 A1 and DE 102004035107 A1. The systems shown in US 2011/0130310 A1, WO 2007/044699 A1 and DE 102004035107 are all in the context of bioreactor consumable units (i.e. small-scale, disposable devices in which the fluid feed reservoirs, the bioreactor chamber and the pumping element are all contained in a single unit), and each has a closed-loop fluid flow path between the feed reservoir and the bioreactor chamber, with recirculation. For useful simulation at small scale of larger-scale processes, for many applications, such as cell culture processing, the accuracy of the amounts of fluid fed to the bioreactor is very important; small variations from the required amount can result in large variations in the effect on the reactions in the cell culture. Hence, the pulsatile flow from peristaltic pumps, diaphragm pumps, and reciprocating piston pumps is not ideal.

In summary, there is a range of challenges in the development and optimisation of bioreactor based manufacturing processes, including: i) general costs of operation of current systems, even that of small scale systems being prohibitive due to complexity of set-up, labour, capital cost, equipment availability within facilities infrastructure required (steam generation) and high costs of media components per unit volume; ii) lack of directly applicable small-scale systems to model larger bioreactors; and iii) a lack of trained personnel driving the requirement for improved throughput per trained employee.

Accordingly, it is an object of the invention to improve the ease and efficiency of the turnaround between experiment runs in small-scale bioreactor systems, reduce labour requirements, reduce the risk of contamination and increase throughput in laboratories, as well as to ensure accurate dispensing of fluids into the bioreactor.

SUMMARY OF THE INVENTION

According to a first aspect of the invention, there is provided a bioreactor consumable unit comprising:
- a bioreactor comprising a chamber;
- at least one fluid feed container integrally connected with the bioreactor and in fluid communication with the bioreactor chamber; and,
- an integral pumping element configured to enable fluid to flow from the at least one fluid feed container to the bioreactor chamber,
- wherein the or each pumping element comprises a syringe and a valve.

The provision of the bioreactor consumable unit (BCU), having an integral connection between the or each fluid feed container and the bioreactor, as well as the integral pumping element (the syringe and valve; together comprising a syringe pump), greatly eases the set-up for an operator of a bioreactor system into which the unit can be received. This is because there is no need to make the fluid connection(s) between the bioreactor chamber and the fluid feed container(s); they are already integral in the unit. Moreover, by having the pumping element integral with the unit, there is no need to separately connect fluids connections to the pumping element; they are already in place. So, upon insertion of the unit into the system, the pumping element is automatically in a proper position and with proper connections for operation.

As a result, there is no need to provide means, such as tube welding equipment, for making sterile fluid connections at the site where the bioreactor processes are to take place (i.e. at a benchtop facility).

Moreover, this arrangement, and variations thereof, has significant advantages in that the syringe pump allows highly accurate amounts of the fluid to be dispensed into the bioreactor.

Preferably, the valve is an active valve. Through the use of an active valve, bidirectional flow can be achieved and controlled, which enables effective priming of the pumping element, purging air therefrom. Such bidirectional flow is not possible with passive valves.

In one embodiment, the valve comprises a three-way valve, with a first port directly coupled to an outlet at the bottom of the fluid feed container, a second port directly coupled to the syringe, and a third port coupled to the bioreactor via a conduit. The valve preferably includes means for rotation of a rotor for rotation thereof at least between first and second operative positions: the first position placing the fluid feed container and the syringe (pump) in fluid communication; and the second position placing the syringe (pump) and the bioreactor in fluid communication. The rotor may further be rotated to a third operative position in which all of the valve ports are closed.

By having the syringe pump directly connected, via the valve, to the outlet of the fluid feed container, there is minimal deadspace volume between the fluid feed container and the syringe pump, so there is very little priming required. In other arrangements, a significant proportion of air is initially drawn into the syringe with the liquid from the container, and as a result an air and liquid mixture is initially pumped along the conduit to the bioreactor. Such systems thus require a priming/purging step to evacuate the air from the mixture. By close coupling of the syringe to the fluid feed container, the syringe chamber can be filled without a significant proportion of air and pumping of the liquid to the bioreactor through the conduit can start right away.

The means for rotation may comprise a slot within the rotor, for engagement by a mating tongue in a valve actuator. Alternatively, the mating tongue and slot features could be the other way round: the slot being part of the actuator and the tongue being part of the valve rotor. Such an arrangement allows the lowering of the BCU into position from above its associated receiving station, during which process the features engage with one another so as to enable the actuation of the valve rotor once fully in position. Furthermore, the means for rotation may instead comprise a lever arm connected to the rotor.

Preferably, the at least one fluid feed container is rigidly attached to the bioreactor. This ensures that the bioreactor and fluid feed container parts of the BCU are held in a fixed relationship, which helps to align those parts to their respective receiving station portions.

The BCU may preferably include means for agitation of a cell culture within the chamber, which means for agitation preferably comprises a stirrer, which replicates the conditions in larger-scale bioreactors. Alternatively, agitation may be provided by alternative means known to the person skilled in the art. One example of a viable alternative is for the bioreactor chamber to take the form of a wave bag, typically having flexible walls, adapted to agitate the contents when rocked by a suitable mechanism.

Typically, the BCU comprises a plurality of said fluid feed containers and a plurality of associated pumping elements. In typical bioreaction processes, multiple fluid feeds (such as nutrients, acid, base, and anti-foaming agents) are required, so providing the storage and connections for each of these in an integral unit means that no additional connections need to be made in order to set up the system.

The fluid communication between the at least one fluid feed container and the bioreactor chamber is preferably sterile. The BCU may be supplied as a sterile unit ready to be dropped into the benchtop bioreactor system. A sterile filter may be included in the fluid flow path between the pumping element and the bioreactor to further enhance the sterility.

In order to protect against contamination in the fluid flow path, the valve may comprise more than one sealing member separating the fluid flow path from the ambient surroundings. Likewise, the syringe may comprise more than one sealing member separating the fluid flow path from the ambient surroundings.

In an alternative, exemplary embodiment, the at least one fluid feed container is directly connected to the bioreactor chamber via a conduit at least a section of which is resiliently flexible and positioned for engagement by a peristaltic pump to urge fluid to flow through the conduit, and wherein the integral pumping element comprises said section of conduit. With such an arrangement, the flexible section of conduit is accessible and positioned ready for engagement by a peristaltic pump when, in use, the BCU is placed in a cell culture module.

Preferably, the BCU further comprises a conduit guide block, wherein at least the resiliently flexible section of said conduit is located by a respective concave arcuate portion in the guide block, and wherein the section of resiliently flexible conduit and the concave arcuate portion together comprise the pumping element. With such an arrangement, the relevant, flexible, part of the conduit is already located in position adjacent the concave arcuate portion, so all that is required in order to pump the fluid is to bring the rotor and rollers of a peristaltic pump into engagement with that part of the conduit, so that it can be pinched against the portion by the rollers as they are turned.

The guide block may include, for the or each fluid feed container: a through passage in which the fluid feed container end of the conduit is received and connected to an outlet of the fluid feed container; and a downwardly projecting foot that includes the concave arcuate portion, wherein the conduit loops under the foot and back up past that portion and beyond, to a point at which the other end of the conduit is connected to the bioreactor chamber. This is a convenient arrangement to place the flexible part of the conduit and the associated portion in a position that can easily be engaged by a peristaltic pump rotor and rollers within the cell culture module.

The bioreactor may further comprise fluid ports for one or more of: connection to gas input supplies; gas output; and chamber contents sample removal.

According to a second aspect of the invention, there is provided a bioreactor system including at least one cell culture module, the or each cell culture module comprising:
- a receiving station for removably receiving a bioreactor vessel consumable unit; and
- a bioreactor consumable unit in accordance with the first aspect received in said receiving station.

The or each cell culture module preferably includes means for actuating the pump element of the associated BCU.

According to the first embodiment, in which the pump element comprises a syringe pump and an associated valve, the means for actuating the pump element preferably comprises an actuator that, when the BCU is received in the receiving station, connects to the plunger of the syringe for moving the plunger into and out of the syringe. Preferably, the actuator and the plunger are configured to connect automatically on insertion of the bioreactor consumable unit into the receiving station. Most preferably, the actuator and the plunger comprise mating snap-fit parts. More preferably, the bioreactor system further comprises a valve actuator for switching the valve at least between first and second operative positions.

According to the exemplary embodiment, in which the pump element comprises the combination of a flexible portion of conduit and an associated concave arcuate portion, the means for actuating the pump element preferably comprises a peristaltic pump that, when the BCU is received in the receiving station, engages with the section of resiliently flexible conduit for urging fluid to flow through the conduit.

Where the valve includes a slot within its rotor, the valve actuator preferably comprises a rotatable tongue configured to engage within the slot of the valve rotor automatically on insertion of the bioreactor consumable unit into the receiving station. Where the valve includes alternative engagement features, as discussed above, the mating engagement features of the valve actuator would be adapted accordingly. As discussed above, these mating features allow the BCU to be inserted from above a receiving station by an operator and for the engagement to take place automatically on insertion, ready for actuation of the valve straight away.

The or each cell culture module typically includes a plurality of receiving stations for removably receiving respective BCUs. In a preferred embodiment, there are two receiving stations on a single module, to receive a pair of BCUs. However, modules may contain just a single receiving station for a single BCU, or any number of receiving stations for respective BCUs. By providing the capacity to accommodate more than one BCU per module, the module may contain elements that can be shared for use with either or both BCUs. By way of non-limiting example, the module may contain a common power supply for supplying electricity to the components for each BCU, such as the stirrer drives or the actuation mechanisms. Likewise, a single processor in the module may control either or both BCU operations.

In this latter regard, the or each cell culture module may include a controller for locally controlling operation of the or each BCU received therein. The bioreactor system may further comprise sensors to monitor parameters of the cell culture in the bioreactor chamber of each BCU, wherein signals from the sensors are communicated to the controller. In this manner, the bioreaction taking place in the bioreactor(s) can be controlled by feedback signals from the sensors. Typically, at least part of the sensors are incorporated into the or each BCU, more particularly in the bioreactor thereof. It is known and convenient to incorporate at least part of a sensor, such as a temperature probe, or a DO sensor spot into a bioreactor, for direct contact with the cell culture therein. With such sensors, they may be interrogated by external sensor readers.

The bioreactor system may further comprise a central module connected to the or each cell culture module for the common supply of one or more of: power; sensor feedback; gas regulation; and control signals thereto for centrally powering and/or controlling operation of the or each associated BCU, and for optional centralised communication output. It is envisaged that multiple cell culture modules may be connected together, either physically or at least communicatively (e.g. via a wireless communication therebetween), so as to be able to run multiple bioreactions in respective BCUs under common power and/or control and taking advantage of the opportunity to share resources across the multiple modules. Even if all the modules are identical, one can be designated as a 'head' or central module, whereby the controller in that module controls at least aspects of the other modules centrally. This may be in conjunction also with local control. For example, the controller of the central module may receive signals from each of the modules and thereby be able to account for common, global, parameters, and adjust operations accordingly, whilst at the same time the local controllers can adjust local operations to account for local conditions specific to the or each BCU in that particular module.

Where the BCU includes a stirrer, the or each cell culture module preferably includes means for actuating that stirrer of the or each BCU received therein, for fully controlled operation of the bioreaction taking place in the BCU within a self-contained module.

The system preferably includes a clamping mechanism for releasably securing the or each BCU in position within the associated receiving station. The clamping mechanism is preferably actuated automatically on detecting the insertion of a BCU, to secure the BCU in place without further operator input.

According to a third aspect of the invention, there is provided a sterile bioreactor consumable unit comprising a bioreactor consumable unit in accordance with the first aspect, in which the or each fluid feed container is loaded with fluid, and the unit is sealed within a sterile package.

Advantageously, such a sterile unit may be prepared in advance and be removed from its sterile package at the point of use, thereby obviating the need to have a sterile environment, such as a laminar flow hood facility, at the point of use within which to load up the unit with the requisite fluids. The sterile units may be purchased from an external supplier.

The principles described herein may be extended to applications other than bioreactors. Many of the advantages associated with having the integral pumping element, such as the ease of set-up and the lack of a need for sterile facilities for making fluid connections between the fluid feed container(s) and the pumping element can be realised independently of the bioreactor.

Accordingly, in accordance with a fourth aspect of the invention, there is provided a consumable unit comprising:
  at least one fluid container; and,
  an integral pumping element configured to enable fluid to flow from the at least one fluid container;
  wherein the pumping element comprises a syringe and a valve.

The conduit volume of the fluid flow path between the syringe and the fluid container is preferably less than the swept volume of the syringe. Further preferably, the combined volume of the fluid flow path through the valve and the volume in the syringe chamber when the piston is fully inserted is less than 1/10th of the swept volume of the syringe. Each of these criteria help to reduce the priming requirements for the syringe pump.

With a conventional arrangement, a liquid reservoir would be connected to the syringe pump valve via a length of tubing. The volume in this tubing can be significant compared with the volume of the syringe chamber and this makes effective priming difficult. To effectively prime these systems, a second tube connection at the valve could be used to return liquid to the liquid reservoir or to waste via a sterile filter. This second tube adds complexity. A contributing factor to the ease of priming is the size of the system, in particular, the diameter of the syringe chamber. When the syringe chamber is 5 mm in diameter or less, then air can be trapped in the chamber by capillary forces. Therefore with small scale systems, where the syringe chamber is 5 mm in diameter or less, particular attention needs to be given to the system design to enable effective priming.

By having the syringe chamber directly connected, via the valve, to the outlet of the fluid feed container there is a very small fluid volume between the syringe chamber and fluid feed container. The arrangement allows for the fluid volume between the syringe chamber and the fluid feed container to be significantly smaller than the capacity of the syringe. Thus, when the syringe initially fills (primes), only a relatively small volume of air could be drawn into the syringe along with a significant volume of liquid. The syringe plunger can be cycled, thereby moving the contents of the syringe chamber back and forth to the fluid feed container. During such cycling of the fluids, air bubbles rise and the air is expelled from the pumping system to the liquid reservoir; the syringe chamber and fluid passageways becoming completely filled with liquid. Once the syringe chamber is purged of air, the system can pump liquid along the conduit to the bioreactor. This arrangement and the priming process avoid air/liquid mixtures being pumped to the bioreactor.

Any combination of two or more of: the syringe body, the valve body and the fluid container can be moulded together as a single unit.

These optional features may equally be employed in the bioreactor consumable unit in accordance with the first embodiment of the first aspect of the invention (the syringe pump embodiment). For example, for the first aspect of the invention, any combination of two or more of: the syringe body, the valve body, the fluid feed container and the bioreactor can be moulded together as a single unit.

And, in accordance with a further exemplary embodiment, there is provided a consumable unit comprising:
  at least one fluid container having an outlet and an outlet conduit connected thereto; and,
  an integral pumping element configured to enable fluid to flow from the at least one fluid container through said conduit;
  wherein at least a section of the conduit is located by a concave arcuate portion and is resiliently flexible, for engagement by a peristaltic pump to urge fluid to flow through the conduit, wherein the section of resiliently flexible conduit and the concave arcuate portion together comprise the pumping element.

The syringe and associated valve on the one hand, and the flexible conduit and associated concave arcuate portion on the other hand, may be as described above in respect of the first aspect of the invention.

According to a fifth aspect of the invention, there is provided a method of priming a consumable unit in accordance with the fourth aspect, comprising the steps of cycling the fluid from the fluid container into the syringe and back into the fluid container. This method may equally be employed with the bioreactor consumable unit in accordance with the syringe pump embodiment of the first aspect of the invention. The advantages of such a method are discussed above.

BRIEF DESCRIPTION OF THE DRAWINGS

The invention will be described, by way of example, with reference to the accompanying drawings, in which:

FIGS. 9a and 9b are schematic side views of a BCU with an integral syringe and valve mechanism according to one embodiment, in which both the valve and the syringe include twin seals, with the syringe plunger shown in respective upper and lower positions;

FIGS. 10a and 10b are respective schematic front and side views of a BCU according to one embodiment, having a slotted rotary valve and a ball-ended plunger;

DETAILED DESCRIPTION

Figure 1B:
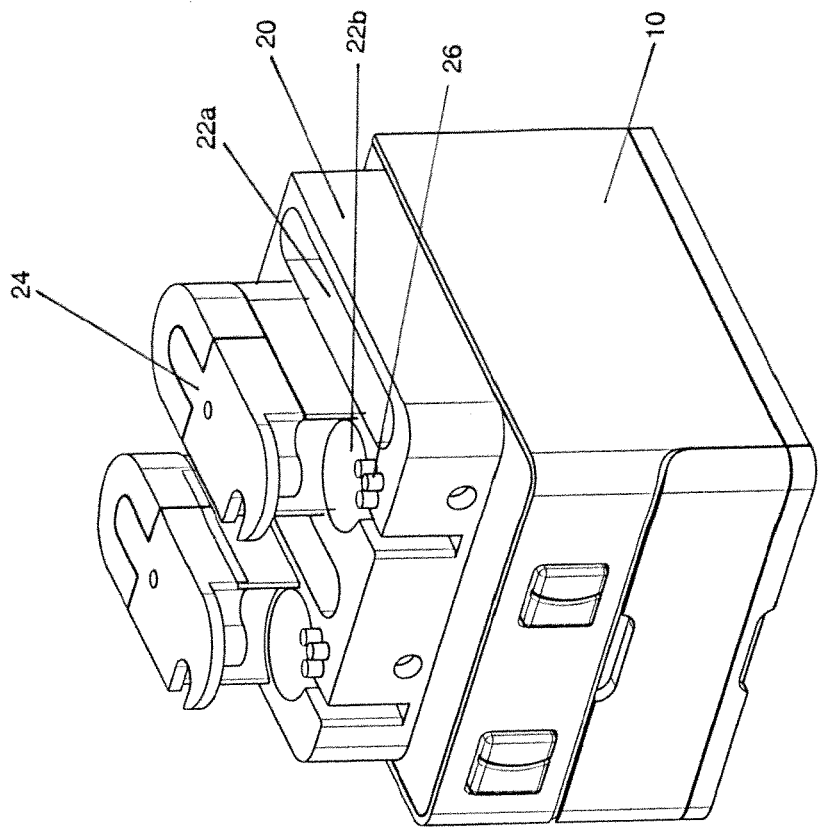
FIG. 1b corresponds to FIG. 1a, but without the bioreactor consumable units.
Figure 1A:
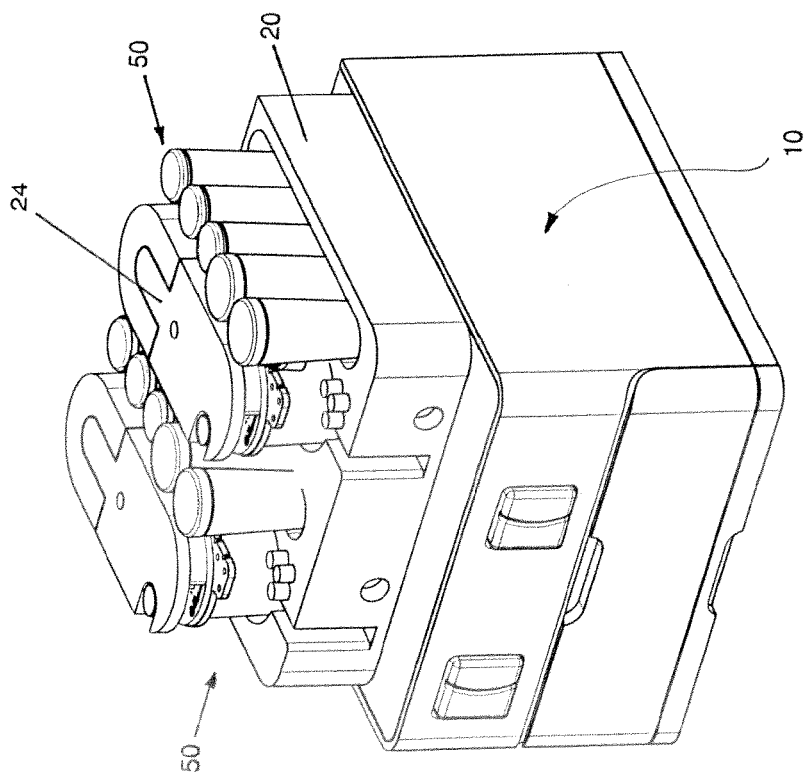
FIG. 1a is a top perspective overview of an automated bioreactor system, with two bioreactor consumable units (BCUs) in situ.

As shown generally in FIGS. 1a and 1b, a cell culture module 10, comprises, generally, a receiving station 20 for removably receiving one or more bioreactor consumable units (BCUs) 50 under respective clamping lid portions 24. In the illustrated embodiment, the receiving station 20 is adapted to receive a pair of BCUs 50, but it will be appreciated that in other embodiments the receiving station could instead be adapted to receive just one or more than two BCUs 50.

The module 10 may be operated as a stand-alone unit (as shown in FIG. 1a) or may be interconnected, physically and/or communicatively, to other such modules to form a larger, modular system (not shown). In such a modular system, one of the modules 10 may be a central or 'head' module, for centrally controlling at least part of the operation of the other modules in the system, as will be described in greater detail elsewhere.

Figure 2:
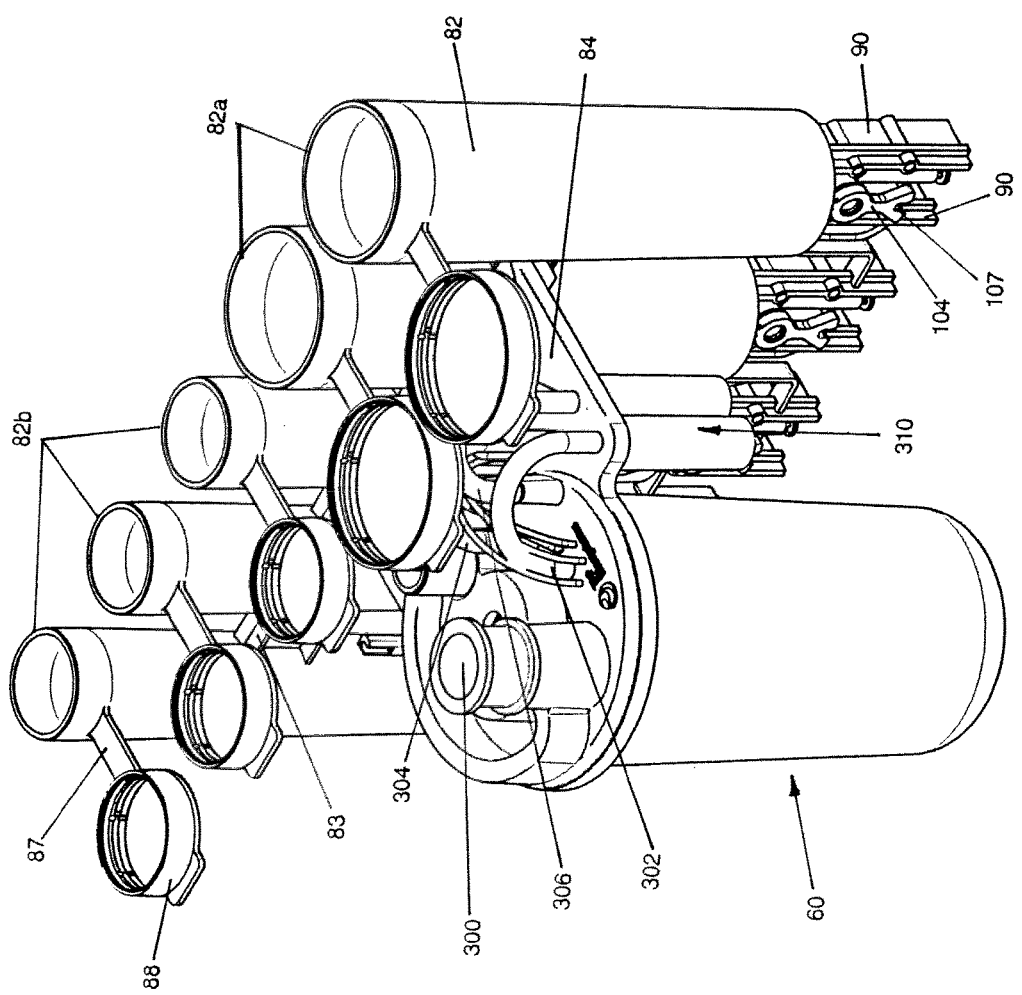
FIG. 2 is a top perspective view of a BCU according to an aspect of the invention.
Figure 3:
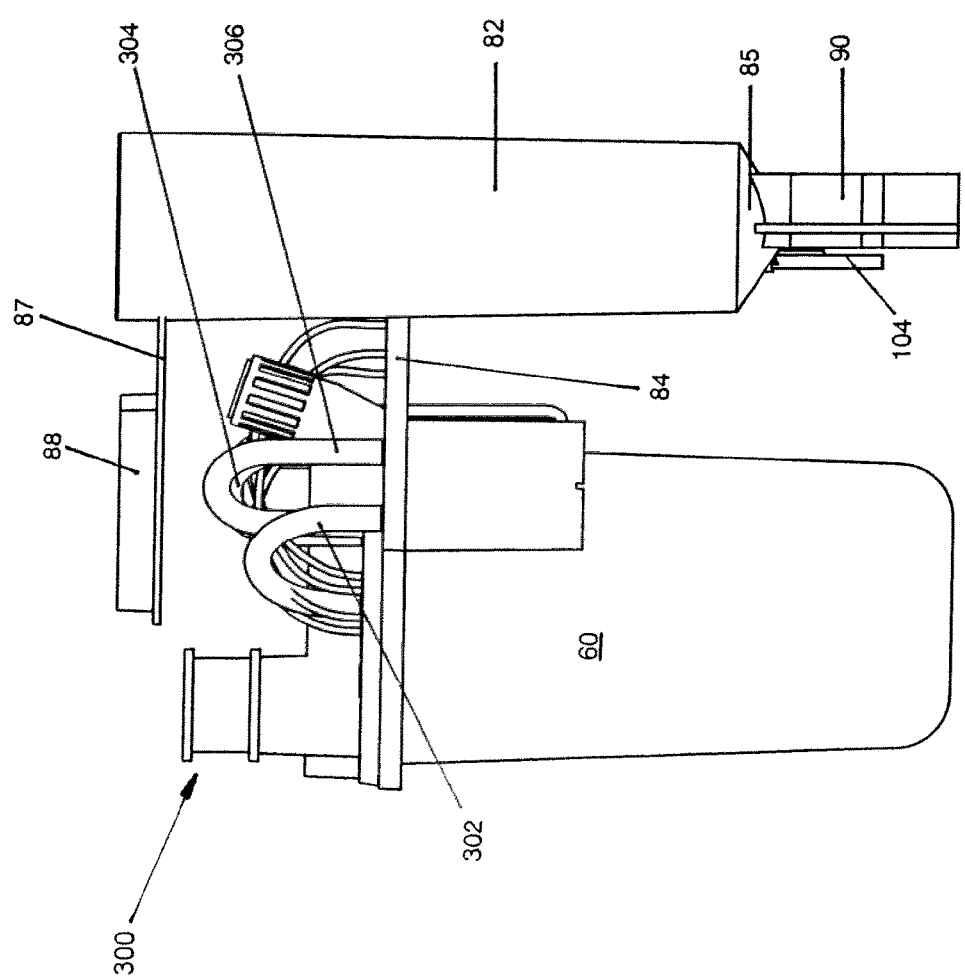
FIG. 3 is a side elevation view of the BCU of FIG. 2.
Figure 4:
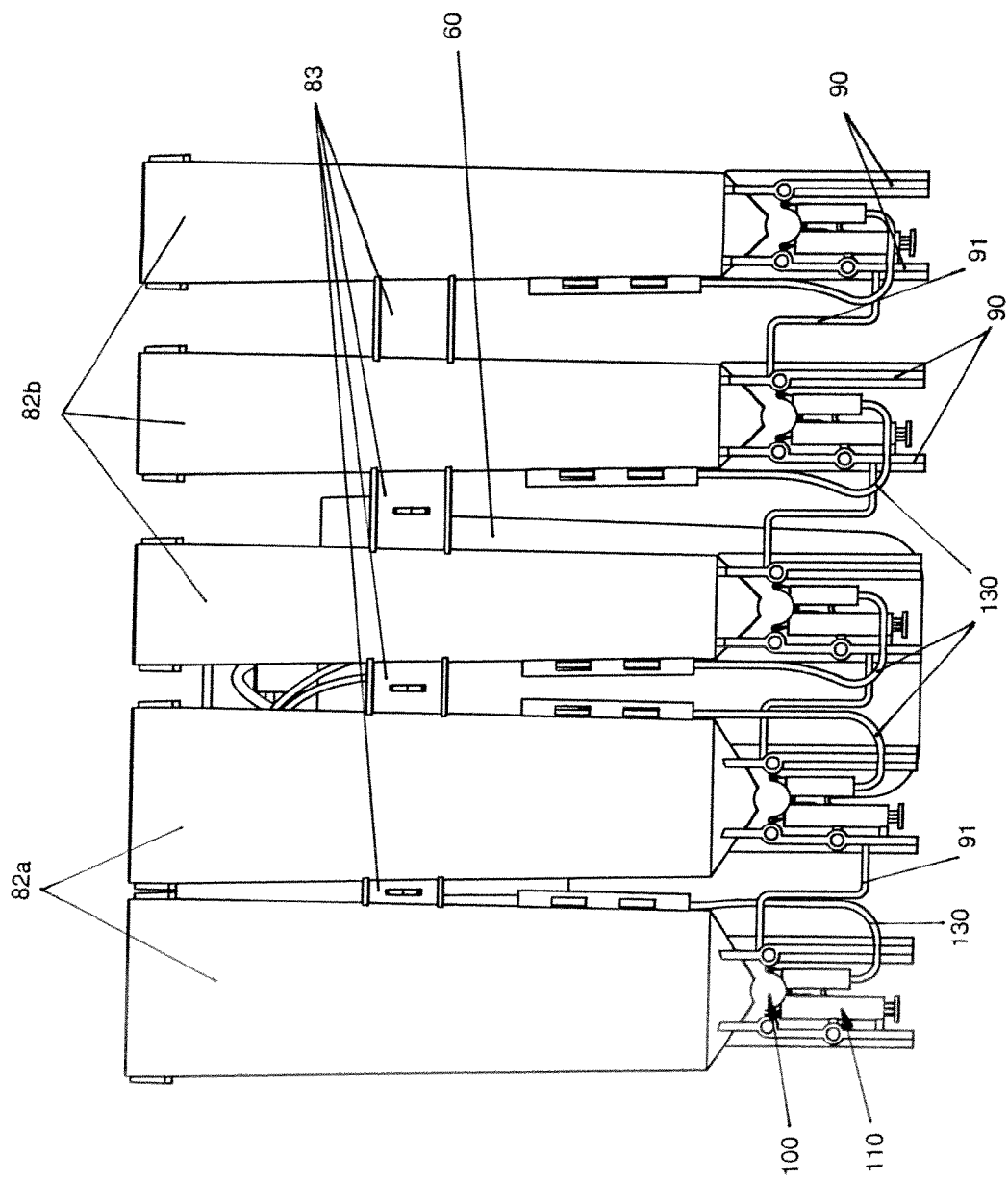
FIG. 4 is a rear elevation view of the BCU of FIGS. 2 and 3.

One embodiment of a BCU 50 is shown in FIGS. 2 to 4. The BCU 50 comprises a bioreactor 60 comprising a chamber 62 and a stirrer 64 (shown in the cross-sectional views of FIG. 5) for agitation of a cell culture 66 in the chamber 62. The bioreactor 60 may be of the type described in the applicant's pending British patent application which has published as GB 2495934 A.

As best shown in FIGS. 2 and 3, the bioreactor 60 includes a filling port 300 for initially admitting the cell culture 66 and for the subsequent extraction of samples of the cell culture 66 during a bioreaction process. Any suitable sample extraction means may be employed. The bioreactor 60 also includes a set of gas lines: typically first and second inlet lines 302, 304, and an outlet line 306, each connected at one end to respective ports into the bioreactor chamber 62 and connected at the other end to a gas filter module 310.

The gas input line 302 is connected to a sparge tube 312 (see FIG. 5) for the delivery of input gases directly into the cell culture 66. The second gas line 304 is for delivery of gases into the headspace above the cell culture 66 in the bioreactor chamber 62. This input line 136 may also include a filter (not shown).

The gas filter module 310 may be respectively connectable to, for example, air, $O_2$, $N_2$ and $CO_2$ gas supplies for selective controlled delivery of those gases, alone or in combination, to the bioreactor chamber 62 via the input lines 302 and 304.

The outlet line 306 is for the passage of exhaust gasses to the gas filter module 310. This outlet line 306 is also provided with a filter, and is typically connected to sensors (not shown) for monitoring the gas composition of the outlet gas to provide an indicator of metabolic activity in the cell culture 66, as described in the introductory portion of the description.

When the BCU 50 is inserted into the receiving station 20, the gas filter module 310 is brought into registration with and connects to upstanding fluids ports 26 on the top of the receiving station 20.

A rack 80 of fluid feed containers 82 is integrally connected with the bioreactor 60 via a rigid bridge 84. As illustrated, the rack 80 includes two larger-bored containers 82a, and three smaller-bored containers 82b, each joined to its neighbour(s) by a beam 83. The larger-bored containers 82a are typically for nutrient feeds and base, whereas the smaller-bored containers 82b are typically for acid, anti-foaming agents and other additives respectively, those being needed in smaller quantities for a typical bioreaction than the nutrients. It will be appreciated, however, that for some reactions one or more of those fluids may not be required, so in those circumstances either some of the containers 82 may be left empty or the rack may be made to suit particular reactions by including only those containers 82a, 82b that are necessary. At its most basic, the rack 80 may contain only a single container 82a for nutrient feed.

Each fluid feed container 82 includes an open topped chamber 81 with a funnel-shaped base 85 having a central outlet 86. A cap 88 is integrally hinged to the upper end of the chamber 81 for closing the open top thereof. The illustrated hinge 87 is a flexible strip of thermoplastic material projecting at one end from a side of the cap 88 and being connected at the opposite end to the fluid container 82. Other hinge arrangements are envisaged. Alternatively, the caps 88 may be separate pieces, but that increases the risk of their becoming lost.

In the embodiment of FIGS. 2 to 4, each fluid feed container 82 includes a pair of legs 90 projecting downwardly from the base 85 for engagement in the receiving station 20; more specifically, in a fluid feed container receiving portion 22a thereof. A brace 91 extends between adjacent legs 90 of neighbouring fluid feed containers 82 to help, with the beam 83, to stiffen the structure. It will be understood, however, that the neighbouring fluid feed containers 82 may be interconnected in other ways, such as being received in a frame, or integrally moulded as a unit. The rack 80 can therefore comprise a single moulding of interconnected containers 82, or may comprise a frame or holder in which separate containers 82 are held.

With reference to FIGS. 1a and 1b, the insertion of a BCU 50 into a receiving station 20 generally comprises raising the clamping lid portion 24 vertically away from the receiving station 20 to clear a path for the BCU 50 to be dropped vertically into place whereby the rack 80 of fluid feed containers 82 is received in the fluid feed container receiving portion 22a and the bioreactor 60 is received in a corresponding bioreactor receiving portion 22b. In one embodiment, the lid 24 is detachable from the remainder of the receiving station 20. Other means for moving the lid portion 24 to clear the path for the BCU 50 are envisaged, including pivoting or sliding arrangements. Also, the path does not have to be vertical but could instead be horizontal or arcuate, or any suitable combination thereof. Once the BCU 50 has been inserted into position, the lid portion 24 can be returned to its clamping position, where it may be held by a clamping screw, for example.

Typically, the clamping lid portion 24 includes a stirrer drive mechanism (not shown) for connection to the stirrer 64 for rotation thereof.

A valve block 100 is located at the outlet 86 of the chamber base 85, between the legs 90. As best seen in the schematic FIG. 5, the valve block includes a three-way valve 102, with an L-shaped rotor 103 rotatable at least between first and second operative positions. A lever arm 104 is connected to the valve 102 for rotation of the rotor. The lever arm has a hole 106 (FIG. 5) or slot (FIG. 2) 107 at a distal end for engagement with an actuating mechanism, to be described in greater detail below. The substantially L-shaped fluid flow path through the rotor 103 is, as illustrated, at about 120 degrees, but it will be understood that any suitable flow path may be employed.

A syringe 110 is connected to the valve block 100. The syringe includes a body 112 and a plunger 114 slidably received therein having a piston 115 at an upper end, and a head 118 at a lower end. A variable volume chamber 116 is defined in the body 112 above the piston 115.

The valve has three ports: a first port 108a in communication with the outlet 86; a second port 108b in communication with the variable volume chamber 116; and a third port 108c that is in communication with the bioreactor chamber 62 by means of a conduit 130. With the valve 102 in the first position (shown in the right-most fluid feed container 82 of FIG. 5), the outlet 86 is in fluid communication with the variable volume chamber 116 of the syringe 110. Accordingly, fluid can be withdrawn from the chamber 81 of that fluid feed container 82 into the variable volume chamber 116 of the syringe as the plunger 114 is retracted.

Figure 5:
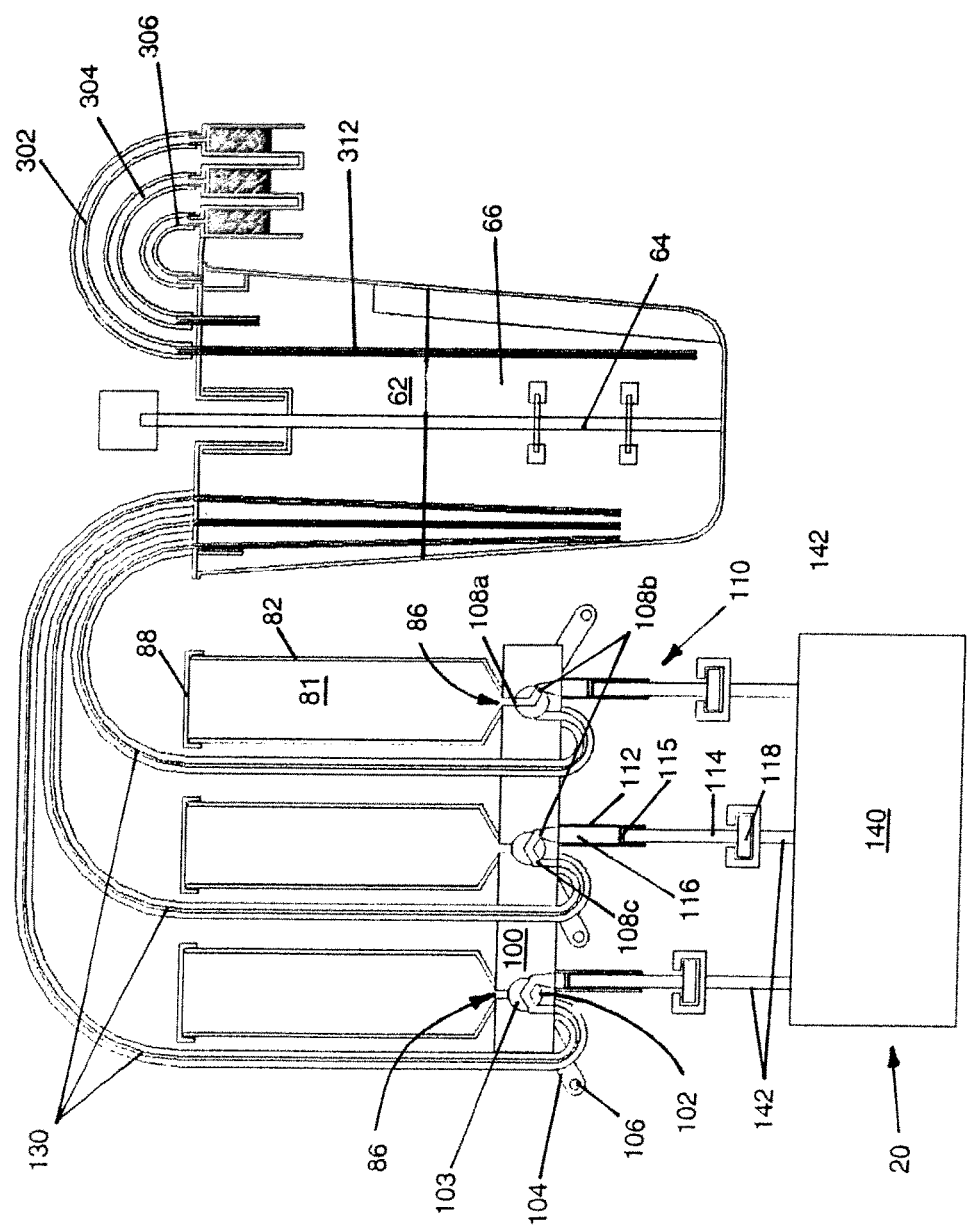
FIG. 5 is a schematic cross-sectional view of a BCU in use connected to a syringe pump actuation mechanism according to one embodiment of the invention.

With the valve 102 in the second position (shown in the left-most and middle fluid feed containers 82 of FIG. 5), the variable volume chamber 116 of the syringe is in fluid communication with the conduit 130 and therefore with the bioreactor chamber 62. Accordingly, as the plunger 114 is urged into the syringe body 112, the contents of the variable volume chamber 116 are displaced to flow along the conduit 130 and into the bioreactor chamber 62. The syringe 110 and the associated valve 102 together comprise a syringe pump.

In a third operative position, all of the valve ports are closed.

In certain embodiments, in order to ensure a sterile fluid flow path between the fluid feed container 82 and the bioreactor chamber 62, both the valve 1102 and the syringe 1110 include twin sealing members, as shown in particular in FIGS. 9a and 9b. The syringe has a first, primary, seal at the piston 1115 and a supplementary, secondary, sealing member 1115a. Likewise, the valve 1102 has both primary and secondary seal members 1103x and 1103y.

It is known that rotary seals can have a little leakage and that linear seals typically have more leakage. Leakage is a significant factor leading to contamination. The intention of the twin seals of these embodiments is to separate the sterile media being pumped from the fluid feed container 82 to the bioreactor chamber 62 from contamination in the atmosphere. The gap between the two seals minimises the chance of atmospheric contamination reaching the pumped media. The gap is typically filled with air but could be any suitable fluid.

The piston 1115 is shown in two positions: the upper position in FIG. 9a and the lower position in FIG. 9b. It is important that the area of the syringe barrel 1112 that the seals travel over do not overlap, because if they were to overlap then the chance of contamination would increase.

The seal member 1115a on the outer or atmospheric seal does not actually need to be a gas tight seal, but rather can be a shield that is effective at blocking (minimising) passage of atmospheric contamination towards the primary seal 1115 at the piston.

As an alternative to a sliding secondary atmospheric seal member 1115a for the plunger 1114, a flexing membrane (not shown) could be applied instead. The chamber created by the membrane may need a sterile vent to prevent excessive pressures as the piston 1115 moves in and out.

For the rotary valve 1102, the seals typically comprise a pair of sealing rings 1103x and 1103y integrally moulded on a stem portion 1103v of the valve rotor 1103 and extending to the inner surface of the surrounding valve housing 1103w. The valve housing 1103w is typically integrally formed with the syringe body 1112 and the fluid feed container 82. The sealing rings 1103x and 1103y may instead comprise O-rings received in respective grooves in the stem portion 1103v. As with the sealing members in the syringe, the outer or atmospheric seal on the valve does not actually need to be a gas tight seal, but rather can be a shield.

It will be appreciated that more than two sealing members can be used to increase the sealing function.

Within the cell culture module 10, and in particular the receiving station portion 20 thereof, a syringe actuator 140, shown schematically in FIGS. 5 and 6, includes displaceable ram 142 connectable to the plunger head 118 of each of the syringes 110.

Figure 6C:
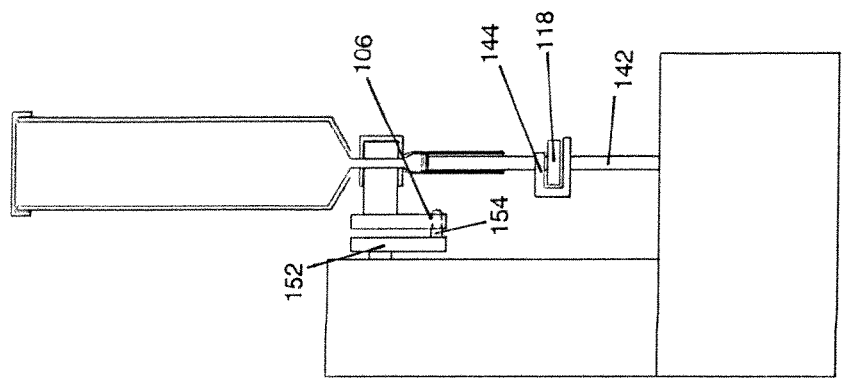
FIGS. 6a to 6c are schematic views of the insertion of a fluid feed container part of the BCU of FIG. 5 being inserted into a receiving station and connected to the syringe pump actuation mechanism and to a valve actuator in accordance with one embodiment.
Figure 6B:
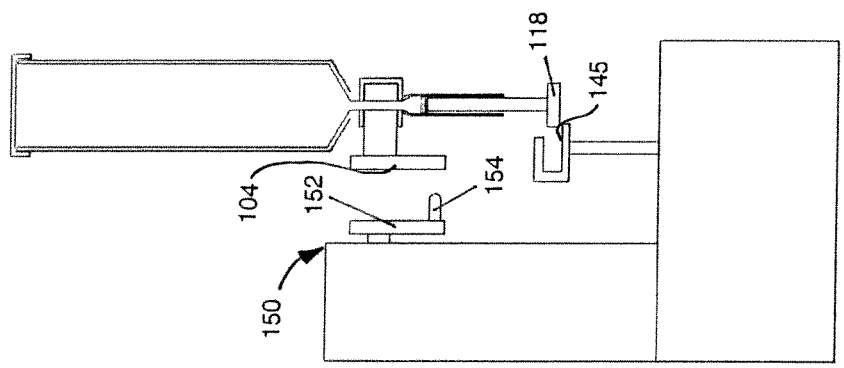
Figure 6A:
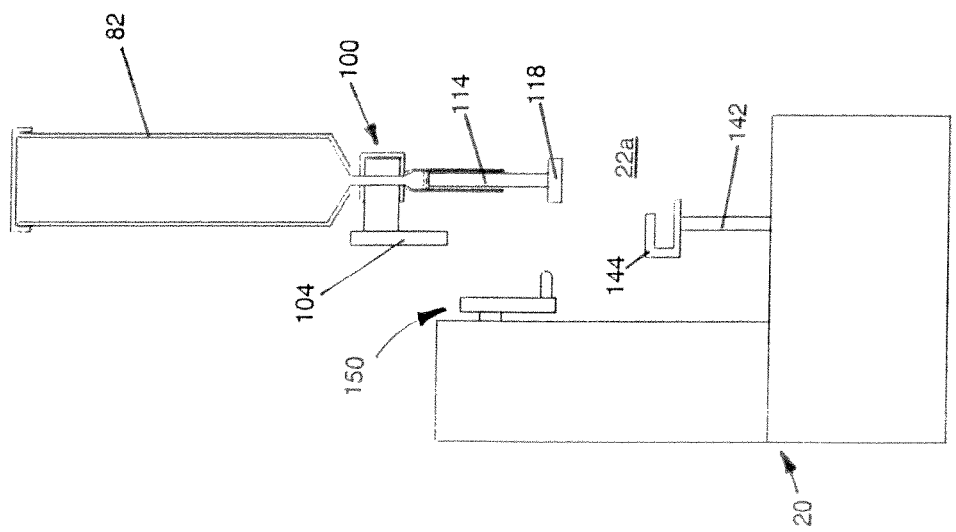

One exemplary mechanism for connecting the end of a ram 142 to the associated plunger head 118 is illustrated in FIGS. 6a to 6c. For clarity, only a single fluid feed container 82 is illustrated, the integrally connected bioreactor 60 being omitted. The legs 90 have also been omitted for clarity. Upon insertion of a BCU into the receiving station 20, the fluid feed container 82 is aligned above the fluid feed container receiving portion 22a and lowered into position (FIG. 6a) until the plunger head 118 is level with a slotted gripper 144 at the end of the displaceable ram 142. It is known that the level has been reached by virtue of the head 118 contacting a lip 145 on the lower part of the gripper 144 (FIG. 6b). The fluid feed container 82 is then translated sideways in the receiving station 20 so that the plunger head 118 is fully received inside the gripper 144 (FIG. 6c). Simultaneously, this lowering and sideways translation movement also brings the valve lever 104 into mating engagement with a rotary valve actuator 150, wherein the sideways translation brings a peg 154 on a rotary drive mechanism 152 of the valve actuator 150 into engagement with the hole 106 or slot 107 in the valve lever 104.

It will be understood that the sideways translation of the fluid feed container 82 relative to the syringe actuator 140 and the valve actuator 150 may instead be achieved by translating the syringe actuator 140 and the valve actuator 150 towards the fluid feed container 82 within the fluid feed container receiving portion 22a.

An alternative mechanism is shown in FIGS. 10 to 12. Instead of the connection between the plunger head and the ram on the one hand and the valve actuator and the valve on the other hand being established via a sideways translation, the connections are made primarily by the vertical insertion of a BCU into the associated receiving station 1140.

Figures 11A, 11B, 11C, 11D:
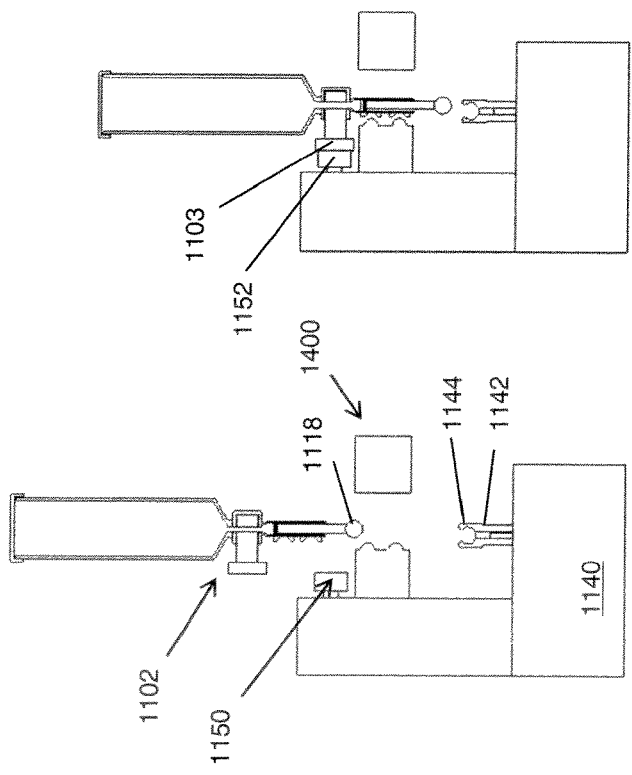
FIGS. 11a to 11d are schematic views of a loading sequence of the fluid feed container part of the BCU of FIG. 10 into the receiving station in accordance with one embodiment.

The insertion process is shown most clearly in FIGS. 11a to 11d. An operator holds the BCU over the receiving station 1140 (FIG. 11a) and then lowers it into place (FIG. 11b). As the BCU is lowered into place, the valve 1102 begins to engage with the valve actuator 1150. In this embodiment, as best seen in FIG. 10a, the valve rotor 1103 includes a vertical slot 1107. The rotary drive mechanism 1152 includes a mating vertical tongue portion that engages with the slot 1107 as the BCU is lowered into place. It can be understood that the mating tongue and slot features could be the other way round: the slot being part of the drive mechanism and the tongue being part of the valve rotor. Any mating features that allow the lowering of the BCU into position from above the receiving station, engaging with one another in the process so as to enable the actuation of the valve rotor once fully in position could be used. By way of example, a pair of pegs could perform the function of the tongue.

A clamp 1400 comprises a stationary first portion 1402 and a second portion 1404 that is translatable horizontally towards the first portion 1402 for clamping the BCU in position. As the clamp 1400 is closed, the BCU, and in particular the syringe part thereof, may be translated a small distance with the second clamping portion 1404 (FIG. 11*c*). This engages the tongue of the rotary drive mechanism 1152 further into the mating slot 1107. The first clamping portion 1402 includes a pair of protrusions 1403*a*, 1403*b*, which engage corresponding grooves 1407*a*, 1407*b* formed in the front side of the syringe body (these grooves being best seen in FIG. 9*b*).

Once clamped in position, the plunger head and the ram are engaged. In this embodiment, the plunger head 1118 is ball-shaped and the ram 1142 has a mating cup portion 1144. The cup portion 1144 engages the plunger head 1118 with a snap-fit connection (FIG. 11*d*). It can be understood that alternative snap-fit connections can be used instead.

The clamping of the syringe and the associated engagement of the valve actuator to the valve and the ram to the plunger preferably occurs automatically upon insertion of the BCU into the receiving station 1140.

Figure 12D:
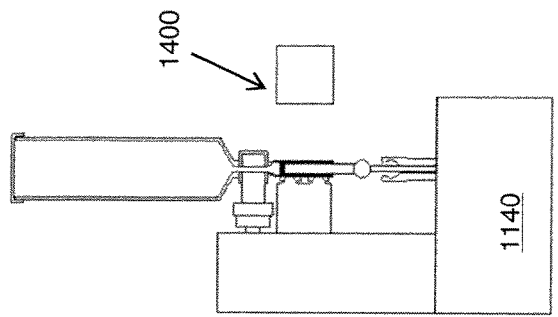
FIGS. 12a to 12d are schematic views of an unloading sequence of the fluid feed container part of the BCU of FIG. 10 from the receiving station.
Figure 12C:
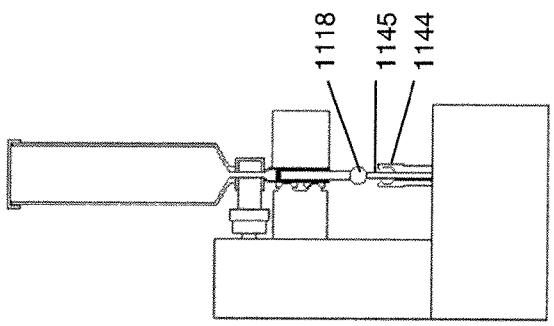
Figure 12B:
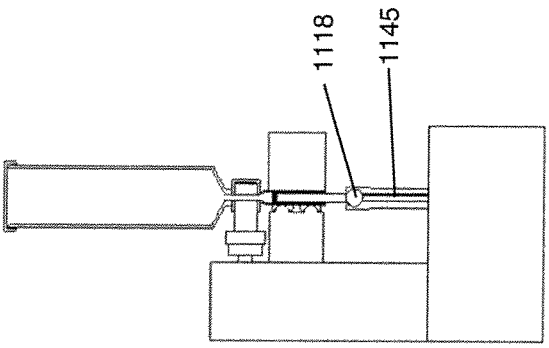
Figure 12A:
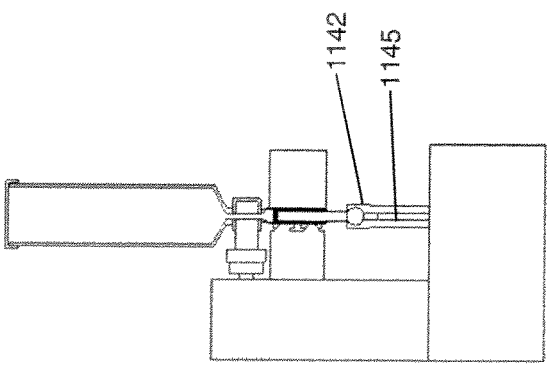

The unloading process is shown in FIGS. 12*a* to 12*d*. FIG. 12*a* in fact corresponds to FIG. 11*d*. The ram 1142 is hollow and includes an ejector pin 1145 vertically moveable relative to the ram 1142 within the hollow centre. The ejector pin 1145 is moved to abut the end of the plunger head 1118 (FIG. 12*b*). The ram 1142 is then retracted, the cup 1144 unclipping from the plunger head 1118 in the process, by virtue of the BCU being clamped in position. The ejector pin 1145 supports the BCU, allowing the clamp 1400 to be released (FIG. 12*d*), thereby enabling an operator to lift the BCU from the receiving station 1140. The abutment of the ejector pin 1145 and the retraction of the ram 1142 could be reversed in order. Moreover, alternative means can be conceived rather than the ejector pin 1145 to support the BCU to allow for the clamp release.

Figure 7:
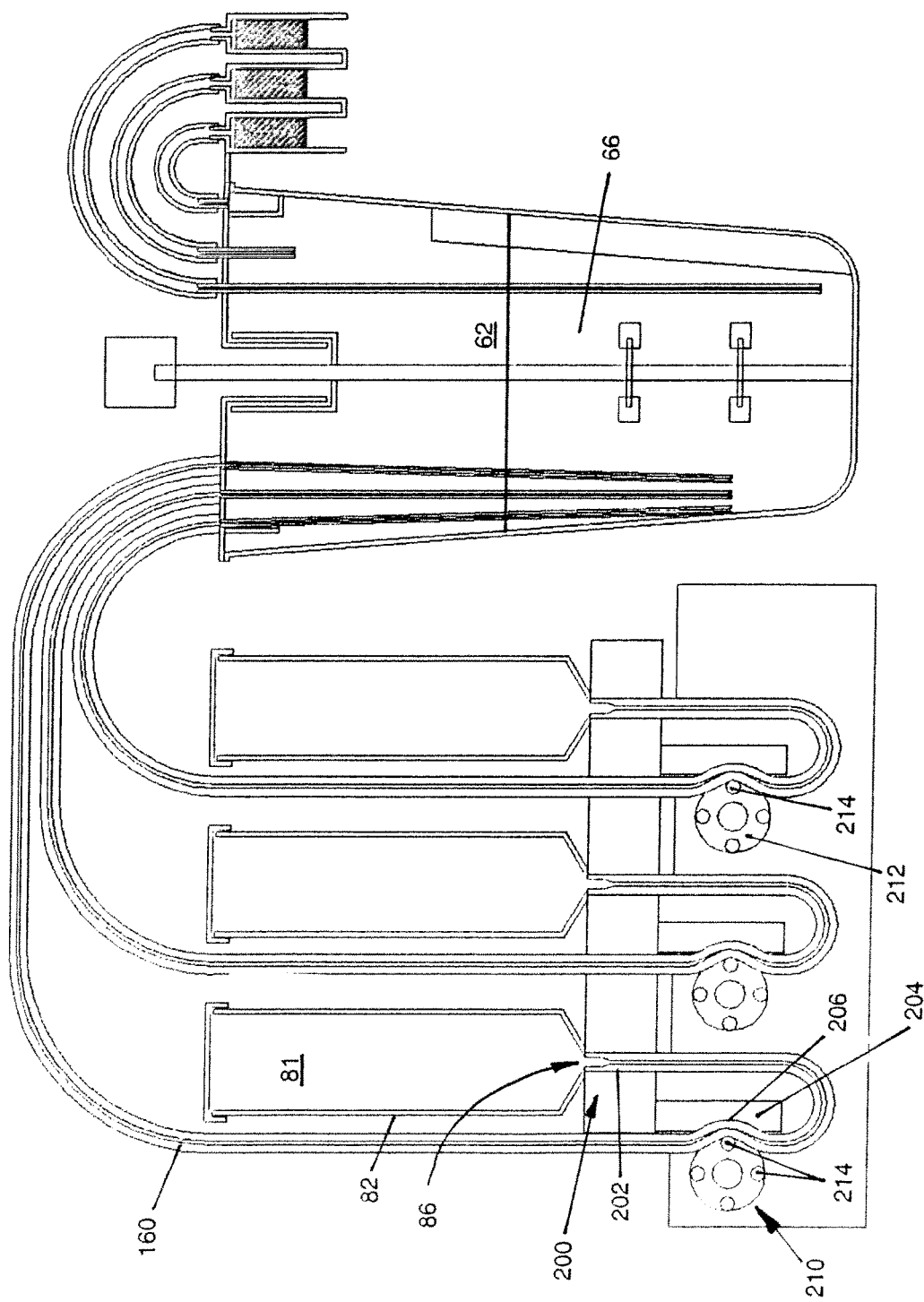
FIG. 7 is a schematic cross-sectional view of a BCU in use connected to a peristaltic pump actuation mechanism according to another embodiment.

In another alternative embodiment of a BCU 500, as shown in FIGS. 7 and 8, the syringe pump arrangement is replaced by a peristaltic pump arrangement, in which the outlet 86 of the fluid feed container 82 is directly connected to the bioreactor chamber 62 via a conduit 160. Instead of the valve block 100, there is a conduit guide block 200 located at the outlet 86 of the chamber base 85. As best seen in the schematic FIG. 7, the guide block 200 includes a through passage 202 in which the fluid feed container end of the conduit 160 is received. The conduit 160 loops under a downwardly projecting foot 204, which includes a concave arcuate portion 206, and back up past that portion 206 and beyond, to a point at which the other end of the conduit 160 is connected to the bioreactor chamber 62.

It will be understood that the concave arcuate portion may, instead of being part of the consumable unit, be part of the cell culture module, more explicitly the receiving station thereof.

In the receiving station 220, a conventional peristaltic pump actuator 210 is located opposite to the portion 206 with the conduit 160 passing therebetween. At least that portion of the conduit is resiliently flexible. The peristaltic pump actuator 210 comprises a rotor 212 with a series of rollers 214 disposed around the periphery thereof. When, in use, the BCU 500 is received in the receiving station 220, as the rotor 212 rotates, the rollers 214 repeatedly compress and release the flexible conduit against the concave arcuate portion 206 behind, whereby the part of the conduit under compression is pinched closed thus urging the fluid within the conduit to be pumped towards the bioreactor 60. Additionally, as the conduit 160 resiliently restores to its natural, open state after the passing of each roller 214, fluid flow is induced.

A tube clamp or valve, preferably a pinch valve, (not shown) would typically be provided to close the liquid path between the fluid feed container and the bioreactor. As shown, when the bioreactor is not engaged with the peristaltic pump, there would be free flow of liquid. The tube clamp could either be manually applied and removed or the valve could be normally closed by spring force and then forced open by the action of loading into the receiving station 22.

Figure 8A:
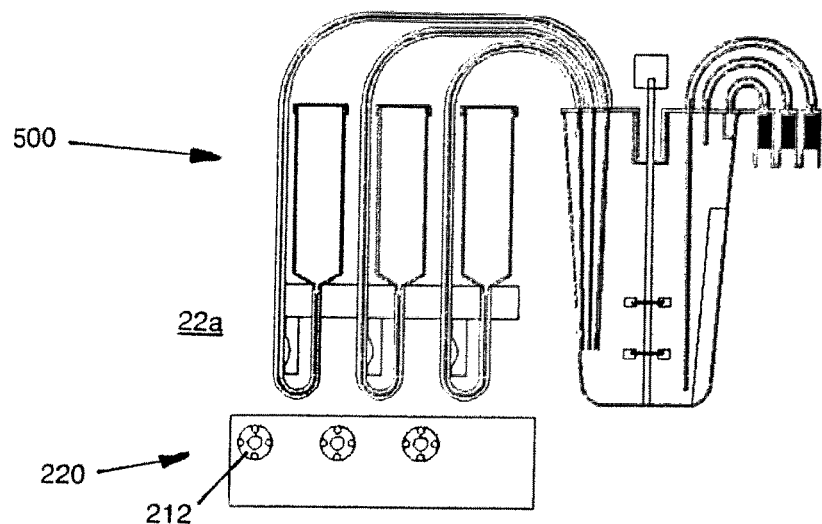
FIGS. 8a to 8c are schematic views of the insertion of a fluid feed container part of the BCU of FIG. 7 being inserted into a receiving station and connected to the peristaltic pump actuation mechanism.
Figure 8B:
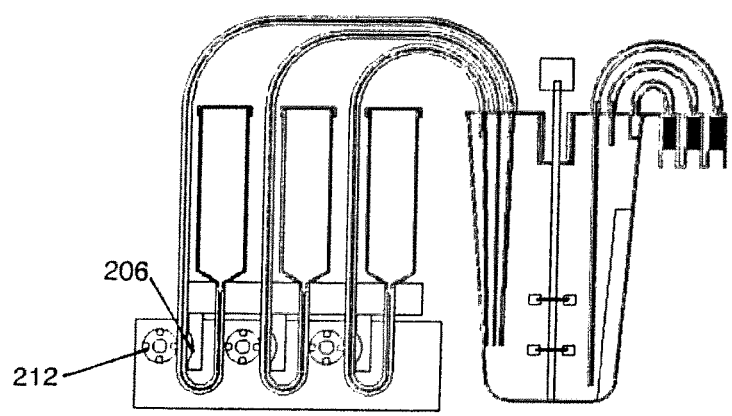
Figure 8C:
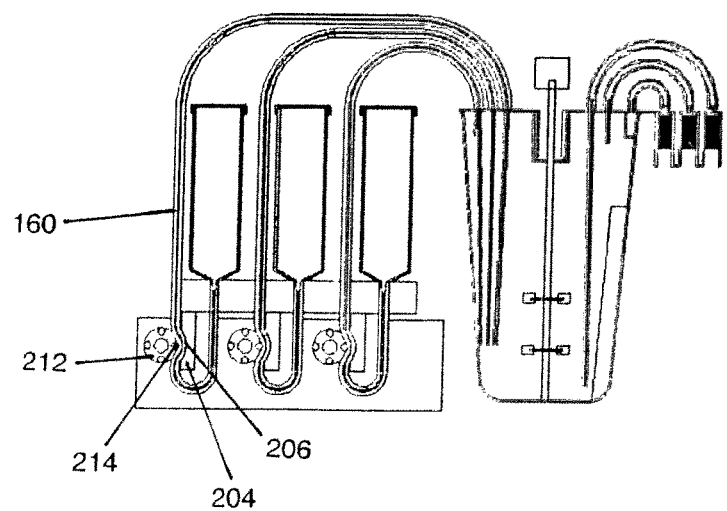

One exemplary mechanism for engaging the peristaltic pump actuator 210 with the associated conduit 160 and concave arcuate portion 206 is illustrated in FIGS. 8*a* to 8*c*. Upon insertion of a BCU 500 into the receiving station 220, the fluid feed container 82 is aligned above the fluid feed container receiving portion 22*a* and lowered into position (FIG. 8*a*) until the concave arcuate portion 206 is level with the rotor 212 (FIG. 8*b*). The fluid feed container 82 is then translated sideways in the receiving station 220 so that the portion of conduit 160 between the rotor 212 and the concave arcuate portion 206 is compressed by one of the rollers 214, or at least would be when the rotor 212 is rotated to bring one of the rollers into the correct position (FIG. 8*c*).

It will be understood that the sideways translation of the fluid feed container 82 relative to the peristaltic pump actuator 210 may instead be achieved by translating the peristaltic pump actuator 210 towards the concave arcuate portion 206 within the fluid feed container receiving portion 22*a*. Where there are multiple rotors 212 for engaging respective multiple conduits 160, the rotors 212 would typically be moved as a set together.

The cell culture module 10 includes a programmable controller for controlling the bioreaction in the bioreactor chamber 62, in particular by controlling actuation of the syringe actuator 140 and of the valve actuator 150 in the first embodiment, or the peristaltic pump actuator 210 of the second embodiment, so as to controllably dispense precise amounts of the liquids in the fluid feed containers 82 into the bioreactor chamber 62 as and when required. Other operations can also be controlled by the controller, such as controlling heaters or chillers, and the control of gases into and out of the bioreactor, but those are outside the scope of the present invention. Typically, the controller would receive feedback from one or more sensors in the system, and the control would be dependent on that feedback. For example, it is known (and described for example in GB 2495934 A.) for sensors to be embedded in the bioreactor 60 itself, sometimes in conjunction with remote sensor readers, to provide indications of the pH level of the cell culture in the bioreactor, or the dissolved oxygen content thereof, or the temperature, etc.

Typically, the BCU is made of a disposable material, for example: a thermoplastic, such as polystyrene or polycarbonate. These are typical materials for a bioreactor vessel that is intended to be disposed of at the end of a cell culture cycle (rather than to be sterilised for re-use). In some embodiments, the valve block 100 and the fluid feed container(s) 82 are moulded together as a single unit. In some embodiments, the valve block 100 and the syringe body (or barrel) 112; 1112 are moulded together as a single unit. In some embodiments, the fluid feed container(s) 82, the valve block 100, and the syringe body 112; 1112 are moulded together as a single unit. In further embodiments, the bioreactor 60 may further be moulded together with any of the above combinations of BCU components as a single unit. 'Moulded together' is intended to encompass other methods of manufacture that can form the individual components together as a single unit (as opposed to making those components separately and then assembling them together), and may, for example, include additive manufacture processes.

In the first embodiment, rather than a pair of legs 90, any suitable structure may be employed to form a portion for receipt in the fluid feed container receiving portion 22a. Preferably, the structure would, like the legs 90, help to protect the valve block 100 and syringe 110 located within.

Rather than being connected via a rigid bridge 84, the fluid feed container(s) 82 may be integrally connected to the bioreactor by other means, which may not be rigid. Rigid is defined as meaning that the interconnected parts are held substantially stationary relative to one another, with little or no flex, although some flex may intentionally be allowed for ease of loading, for example.

As used herein, the term syringe (pump) is intended to encompass not only embodiments in which the piston is slid within the syringe body (or barrel) by means of an attached plunger, but also embodiments where the piston is actuated by other means, such as via magnetic coupling. Common to all embodiments is a variable volume chamber defined by housing walls and by a piston displaceable within the housing.

Rather than a rotary valve actuator 150 and associated lever arm 104, other suitable means for switching the valve between the first and second, and third, operative positions will be known to the skilled reader, with adaption mutatis mutandis to the associated valve actuation mechanism. Also, the skilled person would appreciate that alternative forms of active valve (i.e. operated by an actuator, as opposed to passive valves which open and close dependent on the pressure across the valve) could be used instead. For example, the rotary valve could be replaced by a sliding valve or by a suitable arrangement of pinch valves.

The bioreactor 60 is typically a macro-scale vessel, which is to say it holds a working volume of approximately 250 ml of cell culture solution 66. It will be understood, however, that the principles described with reference to this scale of vessel may be applied, mutatis mutandis, to both larger- and smaller-scale vessels.

The invention claimed is:

1. A bioreactor consumable unit comprising:
a bioreactor comprising a bioreactor chamber;
at least one fluid feed container integrally connected with the bioreactor and in fluid communication with the bioreactor chamber; and,
an integral pumping element configured to enable fluid to flow from the at least one fluid feed container to the bioreactor chamber,
wherein the or each pumping element comprises a syringe and a valve; and
wherein the at least one fluid feed container has a chamber, a chamber base, and an outlet at the chamber base, and the bioreactor consumable unit further comprises a block comprising at least one through passage to guide fluid from the fluid feed container to the pumping element, the at least one fluid feed container being fixedly mounted to the block with the outlet in the chamber base in fluid communication with the through passage.

2. The bioreactor consumable unit of claim 1, wherein the valve is an active valve.

3. The bioreactor consumable unit of claim 1, wherein the valve comprises a three-way valve, with a first port directly coupled to an outlet at the bottom of the at least one fluid feed container, a second port directly coupled to the syringe, and a third port coupled to the bioreactor via a conduit.

4. The bioreactor consumable unit of claim 1, wherein the valve includes means for rotation of a rotor for rotation thereof at least between first and second operative positions: the first position placing the fluid feed container and the syringe in fluid communication; and the second position placing the syringe and the bioreactor in fluid communication.

5. The bioreactor consumable unit of claim 4, wherein the means for rotation comprises a slot within the rotor.

6. The bioreactor consumable unit of claim 1, wherein said at least one fluid feed container is rigidly attached to the bioreactor.

7. The bioreactor consumable unit of claim 1, wherein the bioreactor comprises means for agitation of a cell culture in the chamber.

8. The bioreactor consumable unit of claim 7, wherein the means for agitation comprises a stirrer.

9. The bioreactor consumable unit of claim 1, comprising a plurality of said fluid feed containers and a plurality of associated pumping elements.

10. The bioreactor consumable unit of claim 1, wherein the fluid communication between the at least one fluid feed container and the bioreactor chamber is sterile.

11. The bioreactor consumable unit of claim 10, further comprising a sterile filter in the fluid flow path between the pumping element and the bioreactor.

12. The bioreactor consumable unit of claim 1, wherein the valve comprises more than one sealing member configured to form a gap therebetween that separates the fluid flow path from the ambient surroundings.

13. The bioreactor consumable unit of claim 1, wherein the syringe comprises more than one sealing member configured to form a gap therebetween that separates the fluid flow path from the ambient surroundings.

14. The bioreactor consumable unit of claim 1, wherein the bioreactor further comprises fluid ports for one or more of: connection to gas input supplies; gas output; and chamber contents sample removal.

15. The bioreactor consumable unit of claim 1, in which the fluid feed container is loaded with fluid, and the unit is sealed within a sterile package.

16. The bioreactor consumable unit of claim 1, wherein any combination of two or more of: the syringe body, the valve body, at least one fluid feed container and the bioreactor are moulded together as a single unit.

17. The bioreactor consumable unit of claim 1, wherein priming the bioreactor consumable unit comprises cycling the fluid from the fluid container into the syringe and back into the at least one fluid container.

18. The bioreactor consumable unit of claim 1, wherein the through passage comprises a first opening in fluid communication with the outlet in the chamber base, a second opening in fluid communication with the syringe and a third opening in fluid communication with the bioreactor chamber, and the valve is configured to operate in a first position allowing fluid communication between the first opening and the third opening and a second position allowing fluid communication between the second opening and the third opening.

19. A bioreactor system including at least one cell culture module, the or each cell culture module comprising:
- a receiving station for removably receiving a bioreactor vessel consumable unit; and
- a bioreactor consumable unit in accordance with claim 1 received in said receiving station.

20. The bioreactor system of claim 19, wherein the or each cell culture module includes means for actuating the pump element of the associated bioreactor consumable unit, comprising an actuator that, when the bioreactor consumable unit is received in the receiving station, connects to a plunger of the syringe for moving the plunger into and out of the syringe.

21. The bioreactor system of claim 20, wherein the actuator and the plunger are configured to connect automatically on insertion of the bioreactor consumable unit into the receiving station.

22. The bioreactor system of claim 21, wherein the actuator and the plunger comprise mating snap-fit parts.

23. The bioreactor system of claim 19, further comprising a valve actuator for switching the valve at least between first and second operative positions.

24. The bioreactor system of claim 23, wherein the valve actuator comprises a rotatable tongue configured to engage within a slot of g valve rotor automatically on insertion of the bioreactor consumable unit into the receiving station.

25. The bioreactor system of claim 19, wherein the or each cell culture module includes a plurality of receiving stations for removably receiving respective bioreactor consumable units.

26. The bioreactor system of claim 19, wherein the or each cell culture module includes a controller for locally controlling operation of the or each bioreactor consumable unit received therein.

27. The bioreactor system of claim 26, further comprising sensors to monitor parameters of the cell culture in the bioreactor chamber of each bioreactor consumable unit, wherein signals from the sensors are communicated to the controller.

28. The bioreactor system of claim 27, wherein at least part of the sensors are incorporated into the or each bioreactor consumable unit, in the bioreactor thereof.

29. The bioreactor system of claim 19, further comprising a central module connected to the or each cell culture module for the common supply of one or more of: power; sensor feedback; gas regulation; and control signals thereto for centrally powering and/or controlling operation of the or each associated bioreactor consumable unit, and for optional centralised communication output.

30. The bioreactor system of claim 19, wherein the or each cell culture module includes means for actuating the stirrer of the or each bioreactor consumable unit received therein.

31. The bioreactor system of claim 19, further comprising a clamping mechanism configured to releasably secure the bioreactor consumable unit in position within the receiving station.

32. A consumable unit comprising:
- at least one fluid container integrally connected with the consumable unit; and,
- an integral pumping element configured to enable fluid to flow from the at least one fluid container;
- wherein the pumping element comprises a syringe and a valve; and
- wherein the at least one fluid container has a chamber, a chamber base, and an outlet at the chamber base, and the consumable unit further comprises a block comprising at least one through passage to guide fluid from the fluid container to the pumping element, the at least one fluid container being fixedly mounted to the block with the outlet in the chamber base in fluid communication with the through passage.

33. The consumable unit of claim 32, wherein the conduit volume of a fluid flow path between the syringe and the at least one fluid container is less than the swept volume of the syringe.

34. The consumable unit of claim 32, wherein the combined volume of a fluid flow path through the valve and the volume in the syringe chamber when the piston is fully inserted is less than 1/10th of the swept volume of the syringe.

35. The consumable unit of claim 32, wherein any combination of two or more of: the syringe body, the valve body and the at least one fluid container are moulded together as a single unit.

36. The consumable unit of claim 32, wherein the syringe is connected to the at least one fluid container via the through passage in the block and the valve to achieve a close coupling and a conduit volume of a flow path between the syringe and the at least one fluid container that is minimized, and the conduit volume of a fluid flow path between the syringe and the at least one fluid container is less than the swept volume of the syringe.

37. The consumable unit of claim 32, wherein the through passage comprises a first opening in fluid communication with the outlet in the chamber base, a second opening in fluid communication with the syringe and a third opening in fluid communication with the bioreactor chamber, and the valve is configured to operate in a first position allowing fluid communication between the first opening and the third opening and a second position allowing fluid communication between the second opening and the third opening.

* * * * *